(12) United States Patent
Holmberg et al.

(10) Patent No.: US 6,455,025 B1
(45) Date of Patent: Sep. 24, 2002

(54) POLYSACCHARIDE-PEPTIDE DERIVATIVES

(75) Inventors: Anders Holmberg; Jan-Erik Westlin; Sten Nilsson, all of Uppsala (SE)

(73) Assignee: Map Medical Technologies Oy, Tikkakoski (FI)

( * ) Notice: Subject to any disclaimer, the term of this patent is extended or adjusted under 35 U.S.C. 154(b) by 0 days.

(21) Appl. No.: 09/331,405

(22) PCT Filed: Dec. 22, 1997

(86) PCT No.: PCT/FI97/00827

§ 371 (c)(1),
(2), (4) Date: Oct. 18, 1999

(87) PCT Pub. No.: WO98/28336

PCT Pub. Date: Jul. 2, 1998

(30) Foreign Application Priority Data

Dec. 20, 1996 (FI) .................................................. 965181

(51) Int. Cl.[7] ........................ A61K 38/31; A61K 51/08; C07K 14/655

(52) U.S. Cl. .................. 424/1.45; 424/9.341; 424/9.43; 514/8; 514/11; 514/14; 530/311; 530/322; 530/345

(58) Field of Search ................................. 424/1.1, 1.45, 424/1.69, 9.34, 9.341, 9.411, 9.43, 9.61; 514/23, 8, 9, 11, 14; 530/391.7, 391.9, 311, 322, 345

(56) References Cited

U.S. PATENT DOCUMENTS 5,405,597 A 4/1995 Dean et al. ................ 424/1.69
5,607,659 A * 3/1997 Gustanson ................. 424/1.73

FOREIGN PATENT DOCUMENTS

| WO | WO 90/06949 | 6/1990 |
| WO | WO 92/21383 | 12/1992 |
| WO | WO 95/03330 | 2/1995 |
| WO | WO 96/40792 | 12/1996 |

* cited by examiner

*Primary Examiner*—Jeffrey E. Russel
(74) *Attorney, Agent, or Firm*—Browdy and Neimark, P.L.L.C.

(57) ABSTRACT

Polysaccharide-somatostatin analogs of the formula:

(SEQ ID NO: 1)

[Ala-Gly-Cys-Lys-Asn-Phe-Phe-Trp-Lys-Thr-Phe-Thr-Ser-Cys]   I wherein the somatostatin analog is directly or indirectly coupled from a terminal N-amino group of the somatostatin analog to a polysaccharide, and the polysaccharide-somatostatin analog is provided with an effective negative charge. The compounds are useful in diagnosing and treating cancers.

24 Claims, 3 Drawing Sheets

Effective surface charge as a function of dissociated taurines

STREAMS:

$V^O = 0.62$ ml/h $V^\alpha = 0.48$ ml/h $V^S = 0.47$ ml/h $V^\beta = 0.59$ ml/h $V^C = 0.14$ ml/h SUPPORTING ELECTROLYTE: 0.15 M NaCl
MEMBRANE: MILLIPORE HVLP 0.45 μm
FEEDING TO α-SPACE:
MERE SUPPORTING ELECTROLYTE + PHOSPHATE BUFFER pH 6.8
FEEDING TO β-SPACE:
DEXTRAN A 10 mg/ml + SUPPORTING ELECTROLYTE + PHOSPHATE BUFFER pH 6.8

SEQUENCE LISTING

```
<160> NUMBER OF SEQ ID NOS:  1

<210> SEQ ID NO 1
<211> LENGTH: 14
<212> TYPE: PRT
<213> ORGANISM: synthetic construct
<220> FEATURE:
<221> NAME/KEY: DISULFID
<222> LOCATION: (3)..(14)

<400> SEQUENCE: 1

Ala Gly Cys Lys Asn Phe Phe Trp Lys Thr Phe Thr Ser Cys
1               5                   10
```

POLYSACCHARIDE-PEPTIDE DERIVATIVES

CROSS REFERENCE TO RELATED APPLICATION

The present application is the national stage under 35 U.S.C. 371 of PCT/FI97/00827, filed Dec. 22, 1997.

THE TECHNICAL FIELD

The present invention is related to peptides coupled to charged polydispersive polysaccharides and their radiolabelled derivatives as well as their use in diagnostics and for treatment of cancer and other diseases.

THE BACKGROUND OF THE INVENTION

Technetium-99m is provided with ideal physical properties as a radioactive marker in isotope-imaging. It is easily obtainable from a $^{99}Mo/^{99m}Tc$-generator, which is included in the isotope-laboratory equipment of each general hospital. The methods of labelling peptides with technetium-99m can be divided into two main categories, use of bifunctional metal chelates and use for labelling free thiol-groups. Rhenium, the isotopes $^{186}Re$ and $^{188}Re$ of which are suitable for radiotherapy due to their radiation properties, behaves chemically in the same way as technetium. In addition, many peptides have been labelled for diagnostic and therapeutic purposes with the radioactive isotopes of many other metals by using metal chelates. The most common metal chelates are derivatives of DTPA and EDTA. Further isotopes of halogens, especially iodine, have been used by coupling them to tyrosine and/or histidine residues possibly present in a peptide chain or to separate structures incorporated into the peptide chains.

Due to the general inhibitory effect of somatostatin, it has been tested in treatments of patients suffering from syndromes caused by neuroendocrine tumours. Neuroendocrine cancers are characterized by a large amount of somatostatin-receptors. A crucial problem in medical use of somatostatin is the fact that its biological half-life in blood serum is below three minutes. Due to this fact somatostatin analogs with longer in vivo half-lives have been developed in order to facilitate diagnoses and treatment of neuroendocrine tumours. So far the treatments with somatostatin analogs have mostly been limited to treating hormone-dependent symptoms of the patient.

Radiolabelled somatostatin derivatives are known for example from the following patents/patent applications: U.S. Pat. Nos. 5,225,180; 5,405,597; WO 92/21383 and WO 90/06949.

Successful diagnostic studies have been performed using somatostatin analogs $^{123}$I-Tyr3-octreotide (Lamberts et al., N. Eng. J. Med. 323: 1246–1249, 1990). However, said compound suffers from some disadvantages. It is secreted through the liver-kidney system and thus disturbs the imaging of the lower parts of the body. On the other hand, iodine-123 is an expensive isotope and the labelling technique is complicated.

A ($^{111}$In-DPTA-Phel)octreotide, which is excreted from the body through the kidneys, thus facilitating the diagnoses of tumours inside the stomach without the accumulation of disturbing background-activity, has been developed from the above mentioned somatostatin derivative (Krenning E. P., et al., J. Nucl. Med. 33 :652–658, 1992). Another problem related to the octreotide is also the fact that it does not identify all types of somatostatin receptors. A disadvantage with the use of indium-111 is the fact that it is an expensive isotope and its availability is limited. Indium-111 has to be ordered by the hospital for each patient, separately. In addition, the radiation properties of indium-111 are not well adaptable to diagnostic and therapeutic use.

Somatostatin-dextran (Dextran 10) labelled with technetium-99m has a remarkably longer half-life in blood than native somatostatin($T(1)_{1/2}$=4 h and $T(2)_{1/2}$=8 h) Holmberg, et al., Antibody, Immunoconj. Radiopharm 7: 253–259, 1994).

A further problem related to dextran somatostatin is non-specific binding to the cells, the transfer of the conjugate from the blood circulatory system to the lymphatic system and rather rapid excretion through the kidneys to urine.

THE DISCLOSURE OF THE INVENTION

Analogs of polysaccharide somatostatin with a negative effective surface charge are characterized by non-specific binding. When the transfer of the conjugate to the lymphatic system has been essentially decreased, it has been possible to regulate the transfer of the conjugate through the kidneys to the urine. It has been found that these compounds have special properties in treatment of cancer and they can be radiolabelled for in vivo diagnostics and therapy.

In the present invention the somatostatin analog has been coupled to a soluble polysaccharide with a negative effective surface charge. Hereinafter, said polysaccharides are referred to as charged polysaccharides. In addition, the charged polysaccharide somatostatins can be provided with groups, which in turn are able to bind detecting compounds, such as radionuclides, radiocontrasting substances or paramagnetic ions. Chelation or the production of another in vivo stable bond between the group and the detecting compound is used to carry out the coupling. Hereinafter said groups are referred to as chelates. If the chelate is able to bind only metals, the chelate is referred to as, a metal-chelate. A bond can be formed between the chelate and the detecting group before or after the chelate is coupled to the polysaccharide. It is also possible to couple some compounds directly to the structures of the polysaccharides, in which case a separate chelate is not required. Hereinafter, chelate is written within brackets in order to show that it is also possible to couple the detecting compounds directly to polysaccharides without a chelate. The accordingly formed charged polysaccharide-somatostatin-(chelate)-compounds are capable of binding to somatostatin receptors, which are expressed or over-expressed by tumours and metastases.

Said charged polysaccharide somatostatin (chelate) compounds are hereinafter referred to as the compounds according to the invention.

Compared to previously known methods, it was surprising that with a negative effective total charge a clear decrease in non-specific binding could be obtained and additionally by selecting a suitable polysaccharide size the half-life of the compound according to the invention in blood could be optimized.

A polysaccharide compound with high molecular-weight can be used when it is desired to maximize accumulation into the tumour, but the background concentration is without greater significance. On the contrary, when the background concentration is of importance, as in radiotherapy, the size of the polysaccharide is chosen in such a way that the radiation dose of the critical organ is not exceeded. In said case the size of polysaccharide is optimized in such a way that the accumulation kinetics in the tumour and the elimination of the compound according to the invention produces an optimal radiation dose relation between the tumour and the rest of the organism.

The object is the elimination of the compound according to the invention primarily through the kidneys, in which case the size of the compound should be less than 50 000 g/mol (grams/mole). In many diagnostic applications the background concentration should be low, too. Still, different methods have different clearance times.

One of the essential advantages of the method as compared to known techniques is the fact that it is possible to transport simultaneously to the target cells several somatostatins as well as several radioactive nuclides, if required.

All somatostatin analogs are not capable of identifying all types of somatostatin receptors. In the present invention such a somatostatin analog can be used, which identifies all types of somatostatin receptors or if required a somatostatin analog, which identifies only certain types of somatostatin receptors, thus targeting the compound to find its way to the target cell tissue. The biological half-life in blood is always remarkably dependent on the kind of charged polysaccharide to which the somatostatin analog is bound.

It is generally known that the charge of the polydisperse macromolecule is highly affected by the media in which the macromolecule of interest is situated. Said media dependent so called effective surface charge can deviate remarkably from the theoretical electric charge of the molecule based on the amount of dissociated groups. Said deviation is especially remarkable in a physiological medium, for example, in a human being, injected with said drug.

The evaluation of the effective surface charge is carried out with a multitude of different test systems, in which according to conventional methods based on electrophoresis, give the values, which best describe the actual situation. The effective surface charge can be determined exactly with test system based on convective electrophoresis. Effective surface charges of 10 charge units have been measured on macromolecules.

The polysaccharide can be straight-chained or branched. Preferably, the molecular-weight of the polysaccharide is 10 000–150 000 mol/g. One or more of the hydroxyl groups of the polysaccharide can be substituted independently by other functional groups; as non-limiting examples the following can be mentioned, —COOH, —NHCOCH$_3$, NHSO$_3$H, —OSO$_3$H, —CH$_2$OSO$_3$H, —SO$_3$H. When the radioactive label has been coupled to the polysaccharide it is preferred that the molecular-weight is 30 000– 50 000 mol/g. When a non-labelled charged polysaccharide somatostatin compound is used it is more preferred that the molecular-weight of the polysaccharide is 50 000–80 00 mol/g.

Preferably, the polysaccharide is a polysaccharide formable by one or more different sugar units, with a mutual order which can be dependent or independent of the other. Preferred polysaccharides are dextrans.

In the compounds according to the invention the effective surface charge is obtainable by using compounds having a pKa of 7 or less. More preferred are compounds with a pKa of 4 or less. The following compounds, carboxylic acids and sulphonic acids, can be mentioned as non-limiting examples of such compounds. The charge has preferably been obtained by sulphonic acid groups. The effective surface charge can be 0.0005–1 unit charges per monomer. Preferred is an effective surface charge of 0.001–0.5 unit charges per monomer. Even more preferred is an effective surface charge of 0.002–0.2 unit charges per monomer.

In the compounds according to the present invention the chelate is bound by covalent bonds to the skeleton of charged polysaccharide. One or more chelates can be bound to the charged polysaccharide. Preferably, 0.005–0.5 chelates are bound to the charged polysaccharide per monomer. More preferably 0.05–0.3 chelates are bound to the charged polysaccharide per monomer.

The metal-ion can also be coupled directly to the polysaccharide skeleton. Such a coupling is preferred for technetium and rhenium.

The chelates can be coupled directly or they can be coupled through a bridge or through a mediating molecule to the charged polysaccharide or the somatostatin analog.

The term somatostatin analog includes somatostatins present in nature and analogs and derivatives thereof.

Derivatives and analogs have been used to mean any straight chained or straight-chained cyclic polypeptide derivative, present among somatostatins in nature, in which one or more unit has been removed or substituted by an amino acid radical and/or wherein one or more functional group has been substituted with one or more functional group and/or one or more group has been substituted with another isotheric group. Generally, the term covers all modified biologically active derivatives, which qualitatively fulfill an effect which is similar to that of unmodified somatostatin peptides. For example, they bind to somatostatin receptors or some subtypes of somatostatin receptors to decrease the secretion of hormones.

Cyclic, bridged-cyclic or straight-cyclic somatostatin analogs are known compounds. Such compounds and the preparation there of have been described for example in the European Patent Publications numbers EP 1 295; EP 29 579; EP 215 171; EP 203 031; EP 214 872; EP 298 732; EP 277 419.

Preferred compounds according to the invention are those charged polysaccharide somatostatins, in which the somatostatin analog is $$\overset{\overline{\phantom{AAAAAAAAAAAAAAAAAAAAAAAAAAA}}}{\text{Ala-Gly-Cys-Lys-Asn-Phe-Phe-Trp-Lys-Thr-Phe-Thr-Ser-Cys}} \quad \text{I}$$

(SEQ ID NO:1)

Most preferred compounds according to the invention are those in which the effective surface charge has been obtained with compounds, the structure of which have the formula II and $$W_1\text{—}(W_2)_n\text{—}Z \qquad \qquad II$$

in which:

W$_1$ is a group, which can form an ether, ester or amino bond with a polysaccharide. W$_1$ is preferably an amino group.

W$_2$ is C$_{1-6}$ alkyl, C$_{1-6}$ arylalkyl or C$_{1-6}$ alkyl, C$_{1-6}$ arylalkyl, to the carbon atom of which an optional oxygen atom has been coupled or —NH or —SH or —COOH; -(W$_2$)$_n$ can also be a combination of the groups mentioned above.

n is an integer from 0–7.

Z is COOH or SO$_3$H.

Preferably, W$_1$ is NH and W$_2$ is CH$_2$ and n is 1–3 and Z is SO$_3$H.

Suitable chelate groups are physiologically acceptable chelates, which are capable of binding the detecting element. In addition, a preferred chelate group has a hydrophilic character. Examples of chelating groups are iminodicarboxylic groups, polyaminocarboxylic groups; the following are mentioned as examples of said non-cyclic ligand forming ethylendiaminetetraacetic acid (EDTA), triethylentriaminepentaacetic acid (DTPA), ethylenglycol-0,0'-bis(2-aminoethyl)-N,N,N',N'-tetraacetic acid (EGTA), N,N'-bis (hydroxibenzyl)ethylendiamin-N,N'-diacetic acid (HBED), triethyltetraminehexaacetic acid (TTHA), derivatives thereof, in which one arm is stabilized as in cyclohexan-1, 2-diamin-N,N',N',N'',N''-pentaacetic acid derivatives, derivatives of EDTA and DTPA as for example p-isothiocyanatobenzyl-EDTA or -DTPA, the macrocyclic derivatives thereof, for example 1,4,7,10-tetraazacyclodekan-N,N',N'',N'''-tetraacetic acid (DOTA) and 1,4,8,11-tetraazacyclotetradekan-N,N',N''N N'''-tetraacetic acid (TETA), which are derivatized from N-substitutes or C-substituted macrocyclic amines including cyclamates as described e.g. in EP-A-304 780 and WO-A-89/01476, compounds the structures of which have the form III or IV

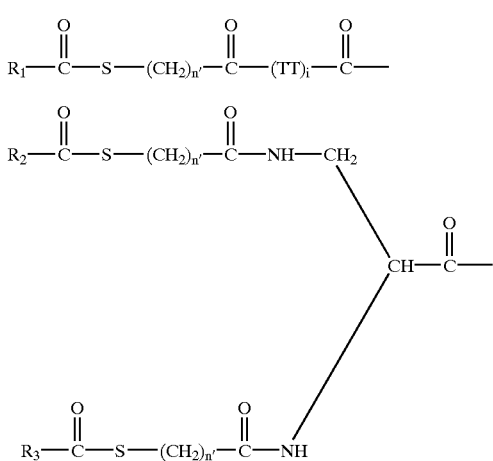

in which
each $R_1$, $R_2$, and $R_3$ are independently $C_{1-6}$ alkyl, $C_{6-8}$ aryl or $C_{7-9}$ arylalkyl, additionally each can also be OH, $C_{1-4}$ alkoxy, COOH or $SO_3H$ substituted
n' is 1 or 2
i is an integer from 2–6 and
TT is independently of each other α- or β-amino acids coupled together with amine bonds.

As examples of chelating groups the following group, which has been Formed from bis-aminothiol derivatives can be mentioned, e.g. compounds with the formula V

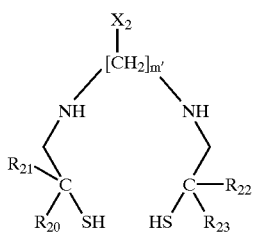

wherein
each $R_{20}$, $R_{21}$, $R_{22}$ and $R_{23}$ are independently of each others hydrogen or $C_{1-4}$ alkyl,
$X_2$ is an amino-, an acid group or a corresponding group, which is capable of reacting with a polysaccharide m' is two or three
compounds, which are derived from dithioazemcarbazone derivatives, e.g. compounds with the structure VI

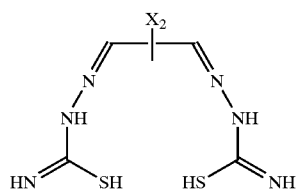

wherein
$X_2$ is the same as above
compounds, which have been formed from amine-oxime derivatives, e.g. compounds having a structure with the formula VII

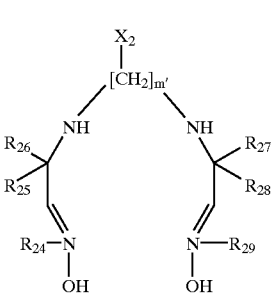

wherein
$R_{24}$, $R_{25}$, $R_{26}$, $R_{27}$, $R_{28}$ and $R_{29}$ are independently H or $C_{1-4}$ alkyl and $X_2$ and m' are as defined above,
compounds, which are diamidedimercaptide derivatives, e.g. compounds of the formula VIII

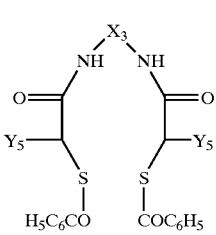

wherein
$X_3$ is a two-valanced radical, optionally substituted and comprising a group which is capable of reacting with a polysaccharide, e.g. $C_{1-4}$ alkylene or phenyl including the group $X_2$ and $Y_5$ is hydrogen or $CO_2R_{30}$, wherein $R_{30}$ is $C_{1-4}$ alkyl
or compounds which are derivatives of porphyrins, such as N-benzyl-5,10,15,20-tetrakis- (4-carboxyphenyl) porphyrine or TPP comprising the group $X_2$ as defined above.

Preferred chelate structures for halogens are compounds with the formula IX

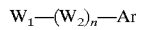

wherein:
$W_1$ is a group, which can form an ether-, ester- or amino-bond with a polysaccharide. Preferably $W_1$ is an aminogroup.

$W_2$ is $C_{1-6}$ alkyl, $C_{1-6}$ arylalkyl or $C_{1-6}$ alkyl, $C_{1-6}$ arylalkyl, to the carbon atom of which an optional oxygen atom has been coupled or —NH or —SH or —COOH; —$(W_2)_n$ can also be a combination of the groups mentioned above.

n is an integer from 0–7.

Ar is an aryl group

It is advantageous if, when $W_1$ is NH and $W_2$ is $CH_2$ n is 1–3 and Ar is benzyl Preferably aryl means phenyl. Aralkyl preferably means benzyl.

Examples of $X_2$ comprise radicals having the form —$(X_4)_{n"}$—$X_5$ wherein $X_4$ is $C_{1-6}$ alkyl; or $C_{1-6}$ alkyl to the carbon-atom of which optionally an oxygen atom has been coupled or —NH—, n" is 0 or 1 and $X_5$ is a group which can form an ether, ester or amino bond with a polysaccharide. It is to be understood that $X_2$ is coupled to the carbon atom of —$[CH_2]_n$— or =CH—CH= by substituting a hydrogen atom.

The chelating group can be coupled directly or indirectly to the polysaccharide. When it is coupled indirectly it is preferably coupled through a bridge or intermediate structure, e.g. a group having the formula X

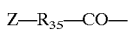    X $R_{35}$ is $C_{1-11}$ alkylene, $C_{2-11}$ alkenyl or —CH(R')—, wherein R' is a residue coupled to the α-carbon in a native or synthetic α-amino acid, e.g. hydrogen $C_{1-11}$ alkyl, benzyl, optionally substituted benzyl, naphthyl-methyl, pyridyl-methyl, Z is a functional group, which can react covalently with the chelate.

Z can or example be a group which can form an ether, ester or amine bond with the chelate. Preferably Z is an amino group.

The chelating group, when it is formed by carboxy, —$SO_3H$ and/or amino groups can be free or in the form of a salt.

Preferred chelating groups are those, which are formed from derivatives of polyaminopolycarboxylic groups, e.g. EDTA, DTPA, DOTA, TETA or substituted EDTA or DTPA.

In the compounds according to the invention the chelating group, when it is polyfunctional, can be coupled either to one polysaccharide molecule or to more polysaccharide molecules.

According to the invention the compounds can exist in free form or in the form of salts. Salts include salts formed from acid, e.g. organic acids, polymeric acids or inorganic acids, of which hydrochlorides and acetates are examples and forms of salts, which are formed from carboxylic groups or sulphonic acids of chelating groups, for example, alkali metal salts such as sodium or potassium or substituted or nonsubstituted ammonium salts.

The present invention is also related to a process for preparing the compounds according to the present invention. They can be prepared using analogs of known techniques.

Compounds according to the invention can be prepared for example in the following way:

Schematic 1

                        1

                        2

                        3 wherein Pa-OH is a polysaccharide unit and $NH_2$—R represents 1) a somatostatin analog, 2) a compound with which a negative surface charge can be obtained as for example taurine 3) a chelate such as N-[2-amino-3(p-aminobenzyl)propyl]-cyclohexane-1,2-diamine-N,N',N',N"-pentaacetic acid (CHXA-DTPA) and tyrosine.

In reaction phase 1 the polysaccharide is activated with $NaIO_4$. In this case the cyclic polysaccharide ring structure is opened. In reaction phase 2 the desired amines and somatostatin are added, which react according to reaction formula 2 with the polysaccharide forming a Schiff bond. In the presence of the cyanoborohydride added in reaction phase 3 an amino bond is further created.

Alternative methods of synthesis have been described in the book Andreas Holmberg, Dextran conjugates for tumor targeting Synthesis and Characterisation, Comprehensive Summaries of Uppsala Dissertations from the Faculty of Medicine 546, ACTA Universitatis Upsaliensis, Uppsala 1995.

The compounds according to the invention can be purified with conventional methods, for example, with chromatography and ultrafiltration.

Preferably the compounds according to the invention comprise less than 5% of the weight of the peptide part of other groups (free chelates, unbound peptide, groups on which an effective surface charged has been obtained).

The compounds according to the invention in the basic form or in their pharmaceutically acceptable form are valuable compounds. As described below a detecting element can be coupled to the compounds according to the invention.

Figure 1:
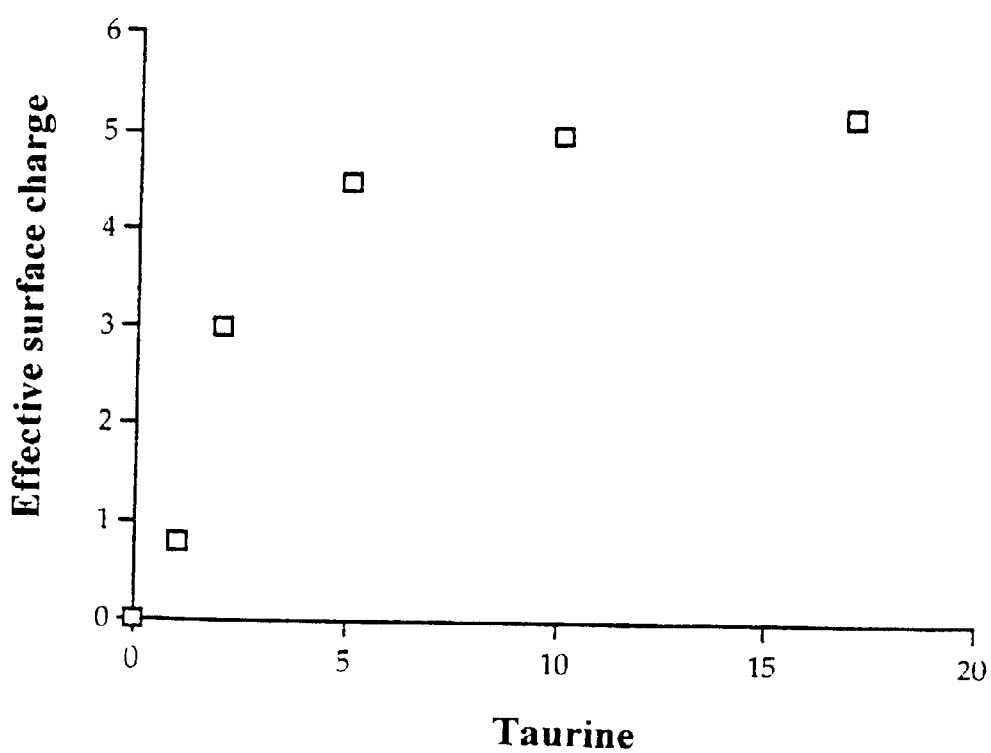
FIG. 1 shows effective surface charge as a function of dissociated taurine.

Accordingly, the present invention comprises the compounds according to the invention which have been defined above, which are complexed to detecting elements (hereinafter referred to as chelates according to the present invention) in free form or in form of salts, the preparation thereof and their use in diagnostics and therapy.

The term detecting element means all compounds, preferably metal ions, which have specific detecting properties in therapeutic or in vivo diagnostic use, for example metallic ions which emit detectable radiation or metallic ions, which have an effect on NMR relaxation properties.

Suitable detecting metallic ions are for example heavy metal elements or rare earth metal ions, for example CAT scanning (Computer axial tomography), paramagnetic ions, e.g. $Gd^{3+}$, $Fe^{3+}$, $Mn^{2+}$ and $Cr^{2+}$, fluorescent metal ions, e.g. $Eu^{3+}$, and radionuclides, e.g. gamma-emitting radionuclides, β-radiating radionuclides, and α-emitting radionuclides as well as positron emitting radionuclides such as $^{68}Ga$.

Radionuclides, which emit gamma-radiation are useful in diagnostics. It is advantageous if the half-lives of said radionuclides are from one hour to 40 days. Preferably, the half-life is from 5 hours to 4 days and most preferably 6 hours to 3 days. As examples of gamma-emitting radionuclides gallium-67, indium-111, technetium-99m, iodine-123, iodine-131, yberium-169, rhenium-186, rhenium-188 can be mentioned. The most preferred gamma-emitting radionuclide is selected taking into account the metabolism of the compound according to the invention and the somatostatin analog which is used.

Also radionuclides which are positron emitters are suitable for recording images.

For therapeutic applications β-particles emitting radionuclides are useful, of these the following can be mentioned: $^{90}$Y, $^{67}$Cu, $^{186}$Re, $^{188}$Re, $^{169}$Er, $^{121}$Sn, $^{127}$Te, $^{143}$Pr, $^{198}$Au, $^{109}$Pd, $^{165}$Dy, $^{32}$P, $^{142}$Pr, $^{166}$Ho, $^{153}$Sm. It is advantageous if the half-life is from 2.3 hours to 14.3 days, preferably from 2.3 hours to 100 hours.

Suitable α-active radionuclides, which can be used in alpha-therapy, are for example, $^{211}$At, $^{213}$Bi, $^{212}$Bi, $^{225}$Ac.

The chelates according to the invention can be prepared by allowing ligands to react with the corresponding detecting element to form the compound. The detecting element can for example be a salt of a metal, preferably a water soluble salt. The reaction can be carried out using analogs of known methods as described in Perrin, Organic Ligand, Chemical Data Series 22. NY Pergamon Press (1982); in Krejcarit and Tucker, Bio-phys. Biochem. Res. Com. 77: 581 (1977) and Wagner and Welch, J. Nucl. Med. 20:428 (1979).

When the compound according to the invention is halogenated, the halogen is coupled to the benzene ring of the chelate using some known halogenation method, which has been described e.g. in Eckelman, Paik and Reba, Cancer Research 40: 3036 (1980).

The metal-chelate combination is preferably obtained in a pH in which the compounds according to the invention are physiologically stable.

The detecting element can be in solution, bound to an intermediate chelate, which enables importation of the detecting element into a physiological pH. Said complex must be thermodynamically more unstable than the ligand-metal complex of the compound according to the present invention. As examples of such intermediate chelates 4,5-dihydroxy-1,3-benzene-disulphonic acid (Tiron), citric-ion, acetate-ion are mentioned. In such a process the detecting element changes ligand.

The chelates according to the invention can be chelated with a metal as described, after which the metal-chelate is coupled to the polysaccharide as described above. In the same way the chelate can be coupled first to a non-detecting metal and then the chelate can be coupled to the polysaccharide and the non-detecting metal later changed to a detecting metallic ion.

The above mentioned reaction can be carried out with analogs of known methods. Depending upon how many chelating groups are present, the efficacy of the labelling can be up to 100%. In such cases no further purification is required. Radionuclids, such as for example technetium-99m can also be in oxide form, for example Tc-99m pertechnetate, which can be complexed in reducing conditions.

The above reactions should be carried out avoiding any impurities. The most advantageous conditions are obtainable using distilled ultrapure water, ultrapure reagents, chelate-class radioactivities, etc. Using the above mentioned reagents the effect of carrier metals can be reduced.

The compounds according to the present invention and their pharmaceutically acceptable salts have pharmaceutical activity and hence they are useful, either as imaging compounds, for example when visualizing somatostatin receptor positive tumours and metastases, when they are complexed with paramagnetic or gamma-emitting metal-ions or positron-emitting radionuclides or radio-drugs when treating in vivo somatostatin receptor positive tumours and metastases with Â- and β-radio-nuclides as shown in the examples. In the examples, it has also been proved that the compounds according to the invention have substantial therapeutic effect without chelating groups and radioactivity. In principal, the compounds according to the invention have affinity to the somatostatin receptors, which tumours and metastases express or overexpress.

Experiments

In the following the invention is described with examples which should not limit the scope of protection Activated Dextran 40 000

20 mg of dextran, the average molecular-weight of which is 40 000 g/mol, and 6 mg sodium periodate were solubilized in 1 ml of sodium acetate buffer pH 5.5. The mixture was incubated for 24 hours at room temperature in dark, mixing with an magnetic mixer. After the incubation, the reaction mixture was purified in a Sephadex G25 column, balanced with 0.2 M sodium phosphate buffer pH 6. The sample was eluted with 2 ml of the same buffer.

Activated Dextran 70 000

Activated Dextran 70 000 was prepared correspondingly using the same method as with activated Dextran 40 000.

Dextran 70 0000 Somatostatin Taurine

Activated dextran 70 000 10 mg, somatostatin analog 1.5 mg (SMSII)

Ala−Gly−Cys−Lys−Asn−Phe−Phe−Trp−Lys−Thr−Phe−Thr−Ser−Cys (SEQ ID NO: 1)

and cyanoborohydride 2 mg were mixed to obtain a final volume of 1.1 ml sodium phosphate buffer pH 6.0. The mixture was incubated in dark at 5° C. for 5 hours after which 100 μl 0.2 M taurine was added. The solution was incubated under the conditions described over night. Thereafter the conjugate was purified with Sephadex G25 column balanced with 0.15 M sodium chloride and elated with the same solution (v=2 ml).

The peptide concentration of the conjugate was determined spectrophotometrically at 280 nm. The somatostatin (SMSII) concentration was calculated from the absorbance using a standard curve, determined under the same conditions. The obtained relation of somatostatin/Dextran was 3.2.

Dextran 40 000-somatostatin-taurine

Dextran 40 000-somatostatin-taurine, which was prepared as above, gave a somatostatin/Dextran relation of 2.1.

Dextran 40 000-somatostatin-taurine-tyramine

Activated Dextran 40 000 10 mg, somatostatin (SMSII) and cyanoborohydride 2 mg were mixed so that the final volume was 1.1 ml sodium buffer pH 6.0. The mixture was incubated in the dark at 5° C. for 5 hours, and thereafter 100 μl of 0.2 M taurine and 100 μl of 0.1 M tyramine were added. The solution was incubated under the conditions mentioned above overnight. Thereafter, the conjugate was purified on a Sephadex G25 column, which was balanced with 0.35 M sodium phosphate buffer and eluted with the same solution (v=2 ml).

The tyramine concentration in the Dextran 40,000-somatostatin-taurine-tyramine compound was determined by first determining somatostatin concentration before the addition of tyramine. The change in the absorbance was subtracted from the absorbance of the final product. Tyramine/Dextran relation was 5.7.

$^{99m}$Tc-Dextran 40 000-somatostatin-taurine

10 μg of SnCl in 10 μl of ethanol was added to Dextran 40 000-somatostatin-taurine 5 mg/ml in one milliliter of 0.9% NaCl. 1500 MBq of sodium pertechnetate was added immediately and the bottle was turned upside down once, to allow the solutions to mix. The bottle was incubated for 15 minutes without mixing. The conjugate was purified with a Sephadex G25 column, which was balanced with a solution of 0.9% NaCl and the product was eluted with 2–3 ml of the same solution. The product was sterilized with filtration. The labelling efficacy was 98.5%.

Dextran 40 000-somatostatin-taurine-$^{131}$I-tyramine 0.5 ml of 0.1 M HCl and 60 μg Kloramine T was added to a solution of Dextran 40 000-somatostatin-taurine-tyramine 5 mg/ml in one milliliter of 0.35 M phosphate buffer pH 7.5 was mixed and transferred to a bottle, which contained 6 GBq $^{131}$I-solution in 0.5 ml 0.1 M NaOH. The mixture was mixed thoroughly and was incubated for 10 minutes, was remixed and was allowed to incubate a second ten minutes. Sodium-metabidi-sulphite 3.5 mg, 100 μl was added and mixed. The incubation was continued for 2 minutes. The conjugate was purified with a Sephadex G25 column balanced with a 0.9% NaCl solution and the product was eluted with 2–3 ml of the same solution. The product was sterilized by filtration. The labelling efficacy was 60.7%.

Dextran 40 000-somatostatin-taurine-tyramine

Activated Dextran 40 000 10 mg, somatostatin (SMSII) and cyanoborohydride 2 mg and sodium phosphate buffer pH 6.0 were mixed so that the final volume was 1.1 ml. The mixture was incubated in the dark at 5° C. for 5 hours, and thereafter 100 μl of 0.1 M taurine and 100 μl of 0.1 M tyramine were added. The solution was incubated under the conditions mentioned above over night. Thereafter the conjugate was purified on a Sephadex G25 column, which was balanced with 0.35 M sodium phosphate buffer and eluted with the same solution (v=2 ml).

Dextran 40 000-somatostatin-taurine-CHXA-DPTA

Activated Dextran 40 000 10 mg, somatostatin (SMSII) and cyanoborohydride 2 mg and sodium phosphate buffer pH 6.0 were mixed so that the final volume was 1.1 ml. The mixture was incubated in the dark at 5° C. for 5 hours, and thereafter 100 μl 0.1 M taurine and 100 μl of 0.1 M N-[2-amino-3(p-aminobenzyl)propyl]-cyclohexane-1,2-diamine-N,N',N',N",N",-pentaacetic acid were added. The solution was incubated under the conditions mentioned above overnight. Thereafter a change of buffer was performed from 20 mM NaAc to 150 mM NaCl buffer in an Amicon concentrator. The method has been described in more detail in Nikula et al., Nucl. Med. Biol. 22: 387 (1995).

Dextran 40 000-somatostatin-taurine-CHXA-DPTA-$^{90}$Y

Dextran 40 000-somatostatin-taurine-CHXA-DTPA labelled on a carrier-free $^{90}$Y. A buffer solution pH 4.5 was prepared from 250 μl 0.2 M HCl and 30 μl 3 M ammonium acetate in an Eppendorf tube. 10 mCi $^{90}$YCl 0.04 M HCl 10 μl was added to this solution. 50 μl Dextran$_2$40 000-somatostatin-taurine-CHXA-DTPA was added to the Eppendorf tube and the reaction was allowed to go on for 20 minutes at room temperature continuously mixing and thereafter the reaction was stopped by adding 20 μl 10 mM EDTA-solution. The efficacy of the labelling was 95.6%. The product was purified on a Sephadex G25 column and the purity of the final product was 99%.

Effective Surface Charge

It is generally known that the charge of a polydisperse macromolecule is affected by the medium in which the macromolecule of interest is situated. This media dependent so called effective surface charge can deviate remarkably from the theoretical electric charge of the molecule which is based on the amount of dissociating groups. The difference is especially remarkable in physiological media, for example, in human beings injected with the drug.

The effective surface charge is evaluated by several different test systems, of which the methods based on conventional electrophoresis provide the values best describing the actual situation. The effective surface charge can be determined most exactly with a test system based on convective electrophoresis. On macromolecules 10 charge units of effective surface charges have been measured.

By carrying out two measurements, of which in the first the concentration of the supporting electrolyte (NaCl) is the same in both compartments (0.15 mol/l) and in the other the electrolyte concentration in the different compartments deviate somewhat (0.127 mol/l and 0.103 mol/l) a surface charge and a diffusion coefficient can be determined exactly. It is essential that the concentrations of the supporting electrolytes buffered to pH-value 6.8 correspond well to the physiological medium effecting the charge.

The Surface Charge of Dextran 40 000 and Dextran 70 000

All measurements with the compounds according to the invention were carried out at a temperature 37° C. and with a Millipore HVLP 0.45 μm membrane.

In the measurements it was detected that the efective surface charge is dependent of the amount of taurine groups in the conjugate according to FIG. 1, but is not dependent on the molecular-weight of the dextran-molecule in the conjugate and not on the amount of tyramine and somatostatin groups coupled thereto.

The Effect of Dextran 40 000-somatostatin-taurine on Metabolism

To patients suffering from kidney cancer a positron-emission-tomography (PET) fluoro-18-diglucose ($^{18}$FDG) was carried out before and after Dextran 40 000-somatostatin-taurine administration. Dextran 40 000-somatostatin-taurine 4 mg (somatostatin SMSII about 325 μg) was administered to the patients. The metabolism of the tumour decreased by 25% after the administration.

The Effect of Different Dextran Conjugates on the Tumour Accumulation and Background-activity After the administration of 20 mCi of technetium-99 m, labelled dextran derivative to the patient a gamma-recording was carried out on the patient. From the image, the accumulation of the labelled compound into the tumours and to the other background tissues was evaluated. The compounds of the state of the art were prepared as described in the publication Holmberg et al., Antibody Immunoconj. Radiopharm 7: 253–257, 1994.

|  | Background | Tumour |
|---|---|---|
| ----- State of Art ----- | | |
| Dextran | +++ | – |
| Dextran 10 000 somatostatin-$^{99m}$Tc | +++ | + |
| Dextran 40 000 somatostatin $^{99m}$Tc | ++ | ++ |
| -----The Invention----- | | |
| Dextran 10 000 somatostatin-taurine-$^{99m}$Tc | ++ | + |
| Dextran 40 000 somatostatin-taurine $^{99m}$Tc | + | +++++ |
| wherein | | |
| – | | means no accumulation |
| + | | means little accumulation |
| ++ | | means accumulation |
| +++ | | means clear accumulation |
| ++++ | | means strong accumulation |

Dextran alone did not at all accumulate into the tumour. When the size of dextran increased a clearly improved tumour accumulation was obtained, but the background activity still remained high. Not until the surface of dextran was provided with a negative effective surface charge, the background activity was substantially decreased and the relative tumour accumulation was clearly improved.

Figure 2:
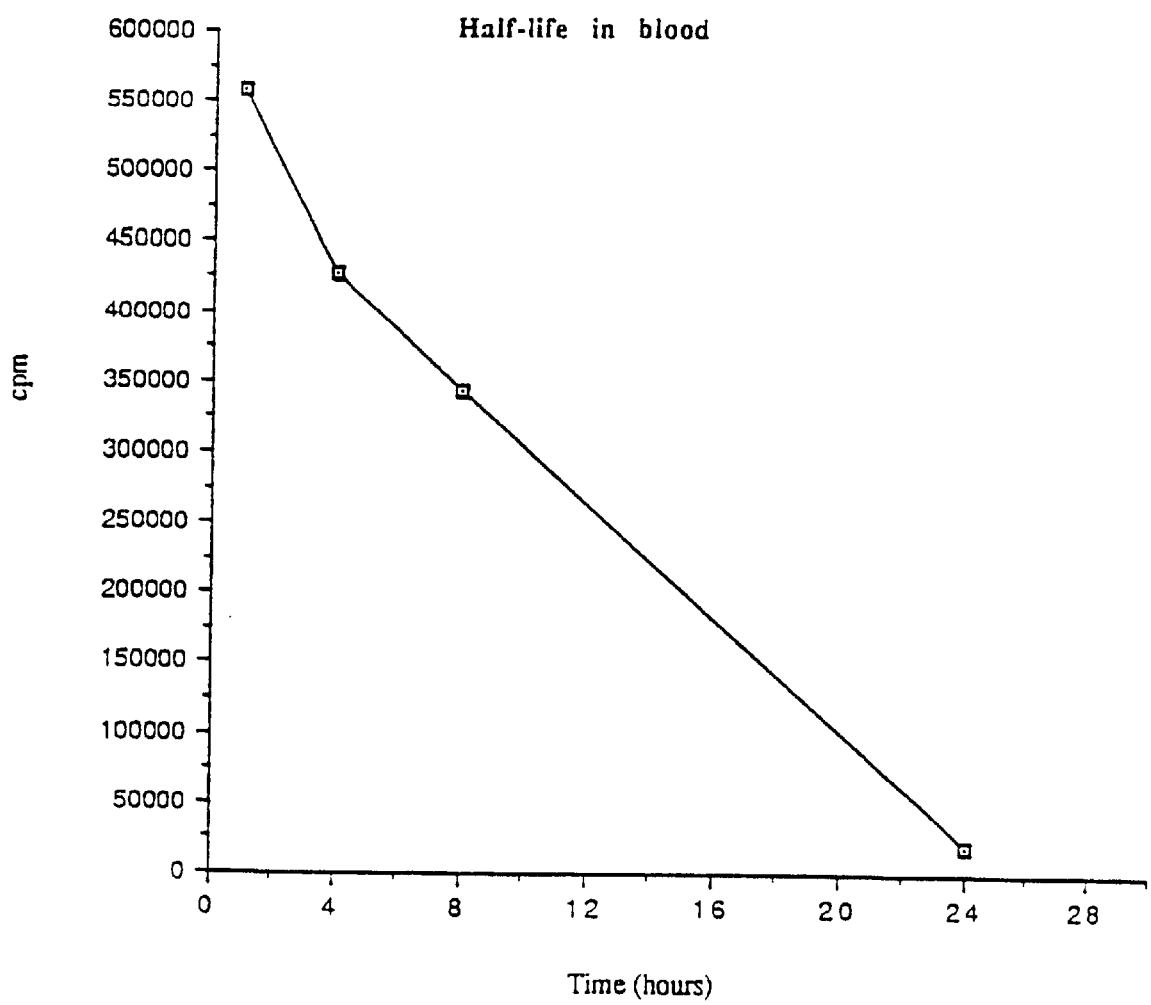
FIG. 2 shows half-life in blood.
Figure 3:
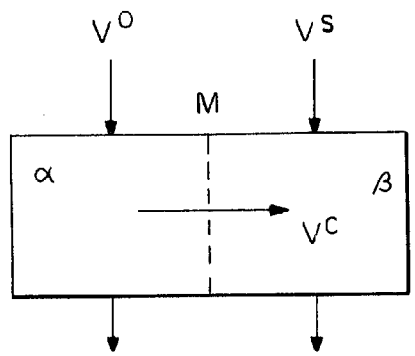
FIG. 3 is a flowchart illustrating determination of the effective surface charge.

The Half-life of Dextran 40 000-somatostatin-taurine-$^{131}$I-tyramine in Blood Patients were administered 3GBq of Dextran 40 000-somatostatin-taurine-$^{131}$I-tyramine and 5 ml blood samples were taken at 4, 8 and 24 hours after the injection. The blood samples were measured on well crystals and the calculation frequency was calculated per milliliter of blood. In FIG. 2 the activity of the samples as a function of time is described. From the Figure it can be calculated that the half-life of Dextran 40 000-somatostatin-taurine-$^{131}$I-tyramine in blood is 12 hours.

3. The compound according to claim 1 wherein $W_1$ is NH, n is 1–3, Z is $SO_3H$, and $W_2$ is $C_{1-6}$ alkyl.

4. The compound according to claim 1 wherein the effective surface charge is provided with taurine.

5. The compound according to claim 1 wherein the effective surface charge is 0.5–10 unit charges as measured by conductive electrophoresis.

6. The compound according to claim 1 which is labeled with a label which is coupled directly to the polysaccharide or to the somatostatin analog.

7. The compound according to claim 6 wherein the label is an inactive label or a radioactive label.

8. The compound according to claim 1 which is labeled with a label, wherein the label is coupled to the compound with a chelate.

9. The compound according to claim 8 wherein the chelate is selected from the group consisting of

What is claimed is:

1. A compound comprising a polysaccharide-somatostatin analog, wherein the somatostatin analog has the formula:

(SEQ ID NO: 1)

[Ala-Gly-Cys-Lys-Asn-Phe-Phe-Trp-Lys-Thr-Phe-Thr-Ser-Cys] I wherein said somatostatin analog is directly or indirectly coupled from a terminal N-amino group of the somatostatin analog to a polysaccharide, wherein said amino group has no significant binding activity to somatostatin receptors, and the polysaccharide-somatostatin analog is provided with an effective surface charge by a group of the formula:

$$W_1-(W_2)_n-Z$$

wherein the pKa of $W_1-(W_2)_n-Z$ is 7 or less and wherein $W_1$ is a group which can form an ether, ester, or amino bond with the polysaccharide;

$W_2$ is at least one of $C_{1-6}$ alkyl or $C_{1-6}$ arylalkyl, optionally coupled to $-NH_2$, $-SH$, or $-COOH$;

n is an integer of from 0–7;

Z is COOH or $SO_3H$; and wherein said group $W_1-(W_2)_n-Z$ provides an effective negative charge to the compound.

2. The compound according to claim 1 wherein $W_1$ is an amino group.

iminodicarboxyl, polyaminocarboxyl, macrocyclic amines, bisaminothiol, dithioacetamidecarbazone, propylene amine oxime, diamidedimercaptan, porphyrin, and salts thereof, and groups of formulas III and IV;

$$R_1-\overset{O}{\underset{\|}{C}}-S-(CH_2)_{n'}-\overset{O}{\underset{\|}{C}}-(TT)_i-\overset{O}{\underset{\|}{C}}- \quad \text{III}$$

$$R_2-\overset{O}{\underset{\|}{C}}-S-(CH_2)_{n'}-\overset{O}{\underset{\|}{C}}-NH-CH_2 \quad \text{IV}$$

$$\underset{\diagdown}{\phantom{x}} CH-\overset{O}{\underset{\|}{C}}-$$

$$R_3-\overset{O}{\underset{\|}{C}}-S-(CH_2)_{n'}-\overset{O}{\underset{\|}{C}}-NH \underset{\diagup}{\phantom{x}}$$

wherein each $R_1$, $R_2$ and $R_3$ is independently $C_{1-6}$ alkyl, $C_{6-8}$ aryl, or $C_{7-9}$ arylalkyl, and wherein each $R_1$, $R_2$ and $R_3$ can optionally be substituted with OH, $C_{1-4}$ alkoxy, COOH or $SO_3H$;

n' is 1 or 2;

i is an integer of from 2–6; and

TT is a combination of an α- or β-amino acid coupled together with an amino bond.

10. The compound according to claim 8 wherein the chelate is selected from the group consisting of derivatives of ethylenediaminetetraacetic acid, triethylenetriaminepentaacetic acid, ethyleneglycol-O,O-bis-(2-aminoethyl)-N,N,N',N'-tetraacetic acid, N,N'-bis(hydroxybenzyl)-ethylenediamine-N,N'-diacetic acid, triethyltetraminehexaacetic acid, cyclohexane-1,2-diamino-N,N,N',N",N"-pentaacetic acid, p-isothiocyanatobenzyl ethylenediaminetetraacetic acid, 1,4,7,0,-tetra azacyclodecan-N,N',N",N"'-tetraacetic acid, and 1,4,8,11-tetraazacyclotetradecane-N,N',N",N"'-tetraacetic acid, and salts thereof.

11. The compound according to claim 8 wherein the chelating group is a compound of formula IX

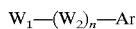     IX wherein
W$_1$ is a group which can form an ether, ester, or amino bond with a polysaccharide;
W$_2$ is C$_{1-6}$ alkyl or C$_{1-6}$ aralkyl to which has optionally been coupled an oxygen atom, —NH$_2$, —SH, or —COOH;
n is an integer of from 0 to 7; and
Ar is an aryl group.

12. The compound according to claim 8 wherein the chelate is coupled to a radionuclide.

13. The compound according to claim 12 wherein the radionuclide is selected from radionuclides which emit α, β, or γ radiation.

14. The compound according to claim 1 wherein the polysaccharide is straight-chained or branched and has a molecular weight of from 10,000–150,000 grams/mole, and optionally at least one hydroxyl group of the polysaccharide can be substituted.

15. The compound according to claim 14 wherein the polysaccharide is substituted with a group selected from the group consisting of —COOH, —NHCOCH$_3$, NHSO$_3$H, —OSO$_3$H, —CH$_2$OSO$_3$H, and —SO$_3$H.

16. The compound according to claim 1 wherein the polysaccharide is dextran having a molecular weight of from 10,000–150,000 grams/mole.

17. The compound according to claim 1 wherein the polysaccharide is dextran having a molecular weight of from 50,000 to 150,000 grams/mole, and the group providing an effective surface charge is taurine.

18. The compound according to claim 17 wherein the dextran-somatostatin analog-taurine is coupled to tyramine which has been labeled with iodine.

19. The compound according to claim 18 wherein the iodine is radioactive.

20. The compound according to claim 19 wherein the iodine is iodine-131.

21. The compound according to claim 17 wherein the dextran is labeled with $^{99}$Tc or $^{188}$Re.

22. The compound according to claim 18 wherein the dextran-somatostatin-taurine compound is coupled to N-[2-amino-3-(p-aminobenzyl)propyl]-cyclohexane-1,2-diamine-N,N',N',N",N"-pentaacetic acid and is labeled with $^{111}$In or $^{90}$Y in basic form or in the form of a physiologically acceptable salt thereof.

23. The compound according to claim 1 wherein the compound is in the basic form or in the form of a pharmaceutically acceptable salt thereof.

24. A pharmaceutical composition comprising a compound according to claim 17 and a pharmaceutically acceptable carrier or solvent.

* * * * *